United States Patent
Keller et al.

(10) Patent No.: US 9,724,382 B2
(45) Date of Patent: Aug. 8, 2017

(54) PHARMACEUTICAL COMPOSITIONS COMPRISING CYCLOSPORIN

(71) Applicant: PARI Pharma GmbH, Starnberg (DE)

(72) Inventors: Manfred Keller, Munich (DE); Aslihan Akkar, Munich (DE); Ralf Mehrwald, Munich (DE)

(73) Assignee: PARI Pharma GMBH, Starnberg (DE)

( * ) Notice: Subject to any disclaimer, the term of this patent is extended or adjusted under 35 U.S.C. 154(b) by 407 days.

(21) Appl. No.: 13/693,147

(22) Filed: Dec. 4, 2012

(65) Prior Publication Data

US 2013/0177626 A1 Jul. 11, 2013

Related U.S. Application Data

(62) Division of application No. 12/086,141, filed on Jul. 28, 2008, now Pat. No. 9,161,963.

(30) Foreign Application Priority Data

Dec. 6, 2005 (DE) .................. 10 2005 058 252
Oct. 31, 2006 (DE) .................. 10 2006 051 512

(51) Int. Cl.
*A61K 38/13* (2006.01)
*A61K 45/00* (2006.01)
*A61K 9/00* (2006.01)
*A61K 9/127* (2006.01)

(52) U.S. Cl.
CPC ............. *A61K 38/13* (2013.01); *A61K 9/0014* (2013.01); *A61K 9/0078* (2013.01); *A61K 9/127* (2013.01); *A61K 45/00* (2013.01)

(58) Field of Classification Search
CPC ...... A61K 38/13; A61K 45/00; A61K 9/0078; A61K 9/127; A61K 9/0014
See application file for complete search history.

(56) References Cited

U.S. PATENT DOCUMENTS

| | | | |
|---|---|---|---|
| 5,006,343 | A | 4/1991 | Benson et al. |
| 5,660,858 | A | 8/1997 | Parikh et al. |
| 5,958,378 | A | 9/1999 | Waldrep et al. |
| 6,465,016 | B2 | 10/2002 | Parikh et al. |
| 7,026,290 | B1 | 4/2006 | Domb |
| 2002/0013271 | A1 | 1/2002 | Parikh et al. |
| 2003/0215494 | A1 | 11/2003 | Knight et al. |
| 2005/0244339 | A1* | 11/2005 | Jauernig ............. A61K 9/0078 424/45 |

FOREIGN PATENT DOCUMENTS

| | | |
|---|---|---|
| EP | 0 294 239 B1 | 12/1988 |
| EP | 0 504 760 | 9/1992 |
| EP | 1 712 220 | 10/2006 |
| WO | 95/24892 | 9/1995 |
| WO | 98/00111 | 1/1998 |
| WO | 98/01147 | 1/1998 |
| WO | WO 98/00111 * | 1/1998 |
| WO | WO 9800111 * | 1/1998 |
| WO | 99/42124 | 8/1999 |
| WO | 00/40219 | 7/2000 |
| WO | 00/45834 | 8/2000 |
| WO | 2005/037246 | 4/2005 |

OTHER PUBLICATIONS

"Baillière's Clinical Gastroenterology, vol. 8, Issue 3, Sep. 1994, Gastrointestinal Transplantation".*

"Massive delayed hemolysis following peripheral blood stem cell transplantation with minor ABO incompatibility by F.M. Laurencet, K. Samii, A. Bressoud, M. Tajeddin, J. Easton, M.J. Stelling and B. Chapuis".*

Unpredictable cyclosporin—fluconazole interaction in renal transplant recipients, Nephrol Dial Transplant. Jul. 1999;14(7):.*

A. Steimer et al., "Cell Culture Models of the Respiratory Tract Relevant to Pulmonary Drug Delivery" Journal of Aerosol Medicine, vol. 18, pp. 137-182 (Nov. 2, 2005).

R. Hughes et al., "Use of Isotonic Nebulised Magnesium Sulphate as an Adjuvant to Salbutamol in Treatment of Severe Asthma in Adults: Randomised Placebo-Controlled Trial", The Lancet, vol. 361, pp. 2114-2117 (Jun. 21, 2003).

K.W. Tsang et al., "Pseudomonas aeruginosa Adherence to Human Basement Membrane Collagen in vitro", Eur. Respir. Journal, 21:932-938 (2003).

M. Knoch et al., "The Customised Electronic Nebuliser: A New Category of Liquid Aerosol Drug Delivery Systems", Ashley Publication, pp. 377-390 (2005).

T.E. Corcoran et al., "Preservation of Post-Transplant Lung Function with Aerosol Cyclosporin", Eur. Respir. Journal, pp. 378-383 (2004).

Klyashchitsky et al., "Nebulizer-compatible liquid formulations for aerosol pulmonary delivery of hydrophobic drugs: Glucocorticoids and Cyclosporine", Journal of Drug Targeting, 7(2), pp. 79-99 (1999).

* cited by examiner

*Primary Examiner* — Snigdha Maewall
(74) *Attorney, Agent, or Firm* — Mintz Levin Cohn Ferris Glovsky and Popeo, P.C.; Peter F. Corless

(57) ABSTRACT

The invention relates to liquid pharmaceutical compositions containing: a) a therapeutically effective dose of a cyclosporin; b) an aqueous carrier liquid; c) a first solubilizing substance selected among the group of phospholipids; and d) a second solubilizing substance selected among the group of non-ionic surfactants. Preferably, the cyclosporin is liposome solubilized. The inventive composition is suitable for oral, parenteral, nasal, mucosal, topical, and particularly pulmonary application in the form of an aerosol.

20 Claims, 2 Drawing Sheets

ID03 2ml

ID04 2ml

PHARMACEUTICAL COMPOSITIONS COMPRISING CYCLOSPORIN

The present application is a divisional of U.S. Ser. No. 12/086,141, filed on Jun. 6, 2008, which was a U.S. national entry application of PCT/EP2006/011459, filed on Nov. 29, 2006.

TECHNICAL FIELD OF THE INVENTION

The invention relates to liquid pharmaceutical preparations which contain ciclosporin as the active agent as well as substances with similar physical, chemical and therapeutical properties and which are suitable for oral, parenteral, nasal, ocular, mucosal, topical and, in particular, for pulmonary application. Further aspects of the invention relate to containers for packaging and applying the preparations and concentrates thereof. Furthermore, the invention relates to the pharmaceutical uses of the preparations and their application for the treatment of specific diseases.

BACKGROUND OF THE INVENTION

Ciclosporin (or cyclosporin) is a cyclic oligopeptide with immunosuppressive and calcineurin inhibitory activity. It is characterised by a selective and reversible mechanism of immunosuppression. It selectively blocks the activation of T-lymphocytes by the production of certain cytokines which are involved in the regulation of these T-cells. This involves, in particular, the inhibition of the synthesis of interleukin-2 which, at the same time, suppresses the proliferation of cytotoxic T-lymphocytes which are responsible, for example, for the rejection of extraneous tissues. Ciclosporin acts intracellularly by binding to the so-called cyclophilines or immunophilines which belong to the family of proteins which bind ciclosporin with high affinity. The complex of ciclosporin and cyclophilin subsequently blocks the serine-threonine-phosphatase-calcineurin. Its activity state in turn controls the activation of transcription factors such as NF-KappaB or NFATp/c which play a decisive role in the activation of various cytokine genes including interleukin-2. This results in the arrest of the immunocompetent lymphocytes during the G0 or G1 phase of the cellular cycle since the proteins which are essential for cell division such as interleukin-2 can no longer be produced. T-helper cells which increase the activity of cytotoxic T-cells which are responsible for rejection are the preferred site of attack for ciclosporin.

Furthermore, ciclosporin inhibits the synthesis and release of further lymphokines which are responsible for the proliferation of mature cytotoxic T-lymphocytes and for other functions of the lymphocytes. The ability of ciclosporin to block interleukin-2 is critical for its clinical efficacy: transplant recipients which tolerate their transplants well are characterised by a low production of interleukin-2. Patients with manifest rejection reactions, on the contrary, show no inhibition of interleukin-2 production.

The first and so far only ciclosporin which has been placed on the market (in the 1980s) is ciclosporin A. Ciclosporin-A is defined chemically as cyclo-[[(E)-(2S,3R,4R)-3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-D-alanyl-N-methyl-L-leucyl-N-methyl-L-leucyl-N-methyl-L-valyl]. Its availability initiated a new era in transplant medicine because, with its help, the proportion of transplanted organs which remain functional in the long term, could be increased substantially.

The first ciclosporin medicament (Sandimmun of Sandoz) could already increase the success rate in kidney transplantations by a factor of about 2. A new oral preparation of ciclosporin (Neoral of Sandoz, later Novartis) with higher and more reliable bioavailability allowed better dosing and further increase of the success rate since the 1990s. Despite some new developments of active agents, ciclosporin is still a frequently used agent in transplantation medicine.

Today, lung transplantations can, in principle also be carried out successfully if patients are treated with ciclosporin A. Since the introduction of this active agent in clinical therapy, the number of lung transplantations carried out worldwide has increased dramatically. This is true for both, the transplantation of a single lung as well as the transplantation of both lungs. Lung transplantations are normally contemplated in the case of patients with a final-staged lung disease where medicinal therapy has failed and life expectancy is short due to the disease. Transplantations of a single lung are indicated, for example, in the case of certain forms of emphysema and fibrosis, such as idiopathic pulmonary fibrosis. Both lungs are transplanted in cases of mucoviscidosis, primary pulmonary hypertension, emphysema with global insufficiency, frequent serious infections as well as idiopathic pulmonary fibrosis with complication by repeated infections.

In the case of a successful lung transplantation, the patients' quality of life can be increased again to an almost normal level. However, contrary to heart, kidney and liver transplantations, the survival times after lung transplantations are still relatively short and amount to an average of only 5 years. This might be due, amongst other things, to the fact that the active agent ciclosporin cannot be effectively dosed with all patients due to systemic side effects such as renal dysfunction, increased serum levels of creatinine and urea, renal damage with structural changes, for example, interstitial fibrosis, increased serum levels of bilirubin and liver enzymes, hypertrichiosis, tremor, fatigue, headache, gingivitis hypertrophicans, gastrointestinal complains like anorexia, abdominal pain, nausea, vomiting, diarrhoea, gastritis, gastroenteritis, paraesthesia, stinging sensations in the hands and feet, arterial hypertension, increased blood fat levels, acne, rashes, allergic skin reactions, hyperglycaemia, anaemia, hyperuricaemia, gout, increasing body weight, oedemas, stomach ulcers, convulsions, menstrual disorders, hyperkalaemia, hypomagnesaemia, hot flushes, erythema, itching, muscular cramps, muscular pain, myopathy, etc.

Therefore, it would be desirable, if, for example, after a lung transplantation or in cases of certain other indications, ciclosporin A could be administered in a targeted and tissue specific fashion and so as to achieve only a low systemic bioavailability of the active agent in order to minimize the impact of the active agent on healthy tissue.

A suitable dosage form could also be used for the treatment and prevention of diseases such as asthma, idiopathic pulmonary fibrosis, sarcoidosis, alveolitis and parenchymal lung diseases (see: Drugs for the treatment of respiratory diseases, edited by Domenico Spina, Clive p. Page et. al., Cambridge University Press, 2003, ISBN 0521773210). New therapeutic aspects also result for the topical treatment of possible autoimmune included diseases such as neurodermatitis, psoriasis, unspecific eczema, skin proliferations or mutations, and for the treatment after skin transplantations. An interesting area of application is in the field of ophthalmology, for example, for the treatment after corneal transplants, of ceratoconjunctivitis or other infectious eye diseases which respond partly insufficiently to anti inflammatory therapy, for example with steroids. It is also useful for the treatment of ceratides in animals, such as dogs.

Indeed, attempts have been made to administer ciclosporin locally, for example, in the form of oily eye drops at 1% and 2% (formulation according to the German codex of medicines using refined peanut oil as solubilizer) or as an aerosol. However, this approach normally fails, mainly due to the very low aqueous solubility of the active agent which renders efficient administration considerably difficult. Thus, in the case of pulmonary application, certain adjuvants for solubilization which may be used in the case of oral administration cannot be employed for lack of tolerability. For example, Sandimmun Optoral capsules (Novartis) which contain ciclosporin A, comprise a microemulsion concentrate with ethanol, propylene glycol and significant amounts of surfactants and, therefore, constitute a formulation which, if inhaled, would cause serious toxic effects.

Similarly, the Sandimmun® infusion solution concentrate (Novartis), which is available for infusion, is also not inhalable: The only adjuvants contained therein are ethanol and poly(oxy ethylene)-40-castor oil. It can be used for infusion only because it is previously diluted with a 0.9% sodium chloride solution or a 5% glucose solution, at a ratio of 1:20 to 1:100. This results in large volumes which can be administered by infusion, but not by inhalation.

WO 00/45834 suggests the inhalation of aerosolized ciclosporin for the prevention or treatment of rejection reactions after lung transplants. It is recommended to administer a dose of 15 to 30 mg of ciclosporin A to the lungs. The carrier to be used for the active agent is propylene glycol which, at such a high concentration, results in considerable irritation, which is why the patients are to inhale a solution of lidocainee for local anaesthesia before administration of the ciclosporin preparation. New research (Akkar et al, poster presentation at NACF 2005) shows that, depending on the concentration, propylene glycol kills calu-3 cells which constitute an established model for lung epithelial cells (Steimer et al. Jour. Aerosol Med. 18 (2) pp. 137-182, 2205). Therefore, for physiological reasons, a predominantly aqueous preparation would be desirable.

EP 0 294 239 A1 describes an aqueous preparation of ciclosporin for pulmonary application. In order to increase the solubility, the preparation contains an α-cyclodextrin. However, the solubilisation effect is far to weak for efficient inhalation therapy: the ciclosporin concentrations achieved are only between 0.1 and 2.0 mg/ml, in particular, between 0.2 and 1.5 mg/ml. This means that, administration of a single dose of 20 mg to the lungs might take hours when using a conventional nebuliser.

EP 0 504 760 A1 describes a special orthorhombic crystalline form of ciclosporin A which is said to particularly suitable for inhalation. However, this would be relevant only for inhalation in powder form or for preparations with a dispersion of the active agent, but not for aqueous solutions for nebulisation. Powder inhalers, however, require a comparatively large breathing volume and are poorly suited for the efficient treatment of patients with pulmonary diseases. Moreover, it is known that amounts of powder >20 mg frequently result in coughing and that the respirable fraction of most powder mixtures decreases with increasing concentration of the carrier, such as lactose or trehalose. Furthermore, in view of all known in vitro data, it seems questionable whether the very poorly soluble active agent, if administered to the lungs in the form of suspended particles, will dissolve in the amount of mucus present in the lungs to a sufficient degree which would be a precondition for therapeutic efficacy. The same is true, in principle, for WO 99/42124 which describes an amorphous liquid crystalline ciclosporin.

WO 95/24892 describes a ciclosporin preparation with propellant gas which is to be applied in the form of a dosing aerosol. However, dosing aerosols have been criticized for years since they contributed to global warming and it seems uncertain whether authorizations to market aerosols containing propellant gases will still be given in the mid term. Similar considerations apply to WO 98/01147. It is also known that the respirable fraction decreases when active agents are applied at concentrations of >1 mg/puff and that the dosing accuracy is subject to large variation in vivo. At a pulmonary deposition of only 10% in the case of dosing aerosols, it can be concluded that more than 50 puffs would be required in order to deposit therapeutically relevant ciclosporin concentrations in the peripheral regions of the lungs.

WO 98/00111 proposes a liposomal dispersion of ciclosporin A for inhalation having a very high concentration of phospholipid of up to 225 mg/ml. However, this has such a high dynamic viscosity that it cannot be nebulised efficiently. A liposomal preparation of ciclosporin A is also known from US 2003/0215494: The invention described therein, however, lies in the fact that such a preparation is to be used for the inhibition of pulmonary metastases. This document does not provide a contribution to solving the technical problem of providing a preparation of the active agent which is more suitable for inhalation. U.S. Pat. No. 5,958,378 describes liposomal ciclosporin preparations for nebulisation; however, the viscosity thereof is so high that these cannot be nebulised with an electronic vibrating membrane nebuliser. Moreover, the organic solvent butanol is used for the preparation thereof, but despite a subsequent lyophilisation process, this cannot be removed completely and yields liposomes of >1 µm, which cannot be sterilized by filtration and which have only a low ability to permeate epithelial cell membranes.

Conventional non-liposomal topical preparations, for example, creams, ointments or lotions, do not show sufficient topical efficacy in the treatment of skin diseases such as neurodermatitis or psoriasis because the effect of penetration is insufficient due to scaling and hornification of the epidermis. It is also known that in some cases of these diseases, even liposomal preparations do not necessarily show improved skin permeation, but, depending on the specific composition and the size and nature of the liposomes, yield only insignificant improvements.

DESCRIPTION OF THE INVENTION

Figure 1:
FIG. 1 shows a typical gamma-scintigraphy image from a patient with double-sided lung transplant after treatment with a radio-labelled dose of the cyclosporine A containing formulation of Example 4, which was nebulised with an electronic vibrating membrane nebuliser of the PARI eFlow 30L type.

It is the object of the invention to provide a ciclosporin containing composition which overcomes the disadvantages encountered in the prior art.

This object is achieved by providing the composition according to claim 1. Further solutions and embodiments result from the other claims.

The composition according to the invention is a liquid aqueous preparation which contains a therapeutically effective dose of a ciclosporin, a first solubility enhancing substance selected from the group of phospholipids and a second solubility enhancing substance selected from the group of nonionic surfactants. A particularly preferred ciclosporin is ciclosporin A.

The composition preferably contains the active agent ciclosporin in a liposomally solubilised form. The liposomes which are formed primarily by the phospholipid contained in the composition are preferably unilamellar liposomes. The liposomes preferably have an average diameter of at most about 100 nm measured as z-average using a Malvern ZetaSizer, and a polydispersity index of at most about 0.5, preferably at most about 0.4.

The liposomes are preferably prepared with water as a carrier liquid and without using organic solvents. The preparation is preferably essentially isotonic and has no negative effect on the transepithelial electrical resistance (TEER) in a calu-3 pulmonary epithelial cell model, which is a measure of the tolerability of the active agent and the formulation in relation to the impact on cellular vitality, and, in human pulmonary cells, the composition does not result in a significant increase of interleukin-8, an inflammation biomarker.

In the context of the present invention, a pharmaceutical composition is a preparation of at least one active agent and at least one adjuvant, which, in the simplest case, can be, for example, a carrier such as water. An active agent is a substance or a mixture of substances which is/are suitable to directly or indirectly promote or support the health or well-being of an animal or human being. An active agent may fulfil a diagnostic, prophylactic or therapeutic function, usually in or on the animal or human body, sometimes, however, in vitro, for example, in contact with isolated body parts such as cells or body fluids.

In the present case, the preparation is preferably a colloidal aqueous solution without organic solvent consisting of unilamellar liposomes having a diameter of at most 100 nm in which the active agent is, at least predominantly, dissolved. Preferably, water is the only liquid solvent contained in the preparation. Furthermore, it is preferred that the preparation is an aqueous solution or an aqueous colloidal solution, i.e., a monophasic liquid system. Such a system is essentially free of dispersed particles having a greater than colloidal particle size. By convention, particles below about 1 μm are regarded as colloidal particles which do not constitute a separate phase and do not result in a physical phase boundary. Sometimes, particles in a size range just above 1 μm are also still considered colloidal. Preferably, however, the invention is essentially free of particles which do clearly not belong to the colloidal spectrum, i.e., for example, particles having a diameter of 1 μm or more.

The composition contains a therapeutically effective dose of a ciclosporin, which is preferably ciclosporin A. Ciclosporin A (or cyclosporin A) is defined chemically as cyclo-[[(E)-(2S,3R,4R)-3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-D-alanyl-N-methyl-L-leucyl-N-methyl-L-leucyl-N-methyl-L-valyl] and is a cyclic peptide with immunosuppressive activity. In this context, the term "therapeutically effective" also includes prophylactic activity. The therapeutic dose is to be defined depending on the individual case of application. Depending on the nature and severity of the disease, route of application as well as height and state of the patient, a therapeutic dose is to be determined in a way known to the skilled person. Some common dosing advice is contained, for example, in the summary of product characteristics for products commercialized under the trademark of Sandimmun® of Novartis Pharma AG, which are also preparations containing ciclosporin A. However, the invention is also to be useful for administering ciclosporin via routes other than the routes of application used so far, in particular, by inhalation after nebulising the preparation with a suitable nebuliser, and it will be necessary to adapt the dosage of the active agent in such applications according to common methods. Furthermore, the preparation according to the invention can, at the same or at a lower concentration, be applied topically or sprayed onto the skin or it can be dropped into the eye or the ear.

Surprisingly, it has now been found that, in an aqueous liquid preparation, ciclosporin can be effectively solubilised and its taste can be masked at the same time by a phospholipid and a nonionic surfactant and that, in certain cases, its stability can be improved. Thus, according to the invention, the preparation contains, apart from ciclosporin and water, phospholipid or a mixture of phospholipids such as, for example, Lipoid S 100 or Phospholipon G90, and a nonionic surfactant, which is preferably a polysorbate, especially polysorbate 80.

This second surfactant acts synergistically with the phospholipid and again increases the real or colloidal aqueous solubility of the ciclosporin contained in the preparation to a statistically significant degree. A surfactant is an amphiphilic or surface-active substance or mixture of substances with surface-active properties. Surfactants have at least one rather hydrophilic and at least one rather lipophilic molecular region. There are monomeric, low molecular weight surfactants and surfactants having an oligomeric or polymeric structure. Furthermore, a distinction is made between ionic and nonionic surfactants. Examples of suitable surfactants within the meaning of the present invention are polyoxyethylene alkyl ethers, polyoxy ethylene sorbitan fatty acid esters such as, for example, polyoxyethylene sorbitan oleate, sorbitan fatty acid esters, poloxamers, vitamin E-TPGS (D-α-tocopheryl polyethylene glycol 1000 succinate) and tyloxapol.

At present, preferred phospholipids are, in particular, mixtures of natural or enriched phospholipids, for example, lecithines such as the commercially available Phospholipon G90, 100, or Lipoid 90, S 100. Among the nonionic surfactants, polysorbates and vitamin E-TPGS are preferred, especially polysorbate 80.

Phospholipids are amphiphilic lipids which contain phosphorus. Known also as phosphatides, they play an important role in nature, especially as the double layer forming constituents of biological membranes and frequently used for pharmaceutical purposes are those phospholipids which are chemically derived from phosphatidic acid. The latter is a (usually doubly) acylated glycerol-3-phosphate in which the fatty acid residues may be of different lengths. The derivatives of phosphatidic acids are, for example, the phosphocholines or phosphatidylcholines, in which the phosphate group is additionally esterified with choline, as well as phosphatidylethanolamine, phosphatidylinositols etc. Lecithins are natural mixtures of various phospholipids which usually contain a high proportion of phosphatidylcholines. Preferred phospholipids according to the invention are lecithins as well as pure or enriched phosphatidylcholines such as dimyristoylphospatidylcholine, dipalmitoylphosphatidylcholine and distearoylphosphatidylcholine.

In a further preferred embodiment of the invention, toxicologically acceptable stabilisers and antioxidants such as sodium ethylene diamine tetraacetic acid (Na-EDTA, tocopheroles), isotonizing adjuvants such as sodium chloride, mannitol, trehalose or buffering salts (citrate, carbonate, phosphate, borate buffers etc.), taste correcting agents such as saccharin, aspartame or mint oil, can be added.

The quantitative composition will usually depend on the medical indication. In general, the chosen content of ciclosporin will range between 0.2 and 20 mg/ml, preferably between about 0.5 and 10 mg/ml, more preferably between about 1 and 5 mg/ml, most preferred between about 1 and 4.5 mg/ml. For the treatment of asthma, lower doses are discussed which may lie in a range of 0.25 to 5 mg/ml. In order to keep the nebulisation time in a compressor, jet or electronic nebulizer such as, for example, the AerX, AeroNeb Go, Omron U22 oder eFlow, as short as possible, it is advantageous to use small volumes of solutions (<2 ml) at higher concentrations. In the especially preferred use of the preparation, i.e., as inhalation solution for the prophylaxis and therapy of lung transplant rejection reactions, it is desirable and, in the interest of sufficient patient compliance necessary that the content of ciclosporin is as high as possible and the inhalation time, thus, as short as possible. Preferably, the content of ciclosporin—especially that of ciclosporin A—should be at least about 0.5 mg/ml, for example, between 0.5 and 10 mg/ml. A content of 1-5 mg/ml is even better and can be achieved by using the features of the present invention. In a further preferred embodiment, the composition has a content of ciclosporin A for the topical application to the skin or for dropping into the eye or the ear of 0.1-2% and for the prophylaxis and treatment of respiratory diseases of 1.5-5 mg/ml or more, for example, a content between about 5-10 mg/ml.

The required content of surface active adjuvants depends on the content of ciclosporin A. If lower concentrations of 0.5-1% of active agent are solubilised, the content of lecithin/surfactant can be proportionally reduced. In general, the phospholipid content in the composition should lie between about 0.2 and about 15 wt.-%, and preferably in the range of about 1 to about 8 wt.-%.

The nonionic surfactant should be present at a concentration of about 0.01 to about 5 wt.-% and preferably the concentration thereof should lie in the range of 0.1 to 2 wt.-%, especially in the case that a polysorbate is selected, for example, polysorbate 80.

The weight ratio of phospholipid or the phospholipid component to the nonionic surfactant is especially important in determining the amount of ciclosporin that can be solubilised per unit volume. A ratio between about 15:1 and 9:1, especially between about 14:1 and 12:1, i.e., for example, in the range of about 13:1, is preferred. These preferred ranges also apply, in particular, in the case that a polysorbate such as, for example, polysorbate 80 is selected as a nonionic surfactant.

The chosen weight ratio between the two solubilising adjuvant components, i.e., the phospholipid and the nonionic surfactant on the one hand and the ciclosporin on the other hand is generally between about 5:1 and about 20:1. In currently preferred embodiments, the ratio is about 8:1 to about 12:1, for example about 10:1. In a particularly preferred composition, the ratio of ciclosporin A to the Lipoid S100/surfactant mixture is 1:9 and the content of solubilised ciclosporin A is up to 0.5 wt.-% which results in the following ratio of mixture: ciclosporin:Lipoid S100:polysorbate 80=1:9:0.69, whereby one obtains unilamellar liposomes with a ciclosporin content of, in total, about 4 to 6 wt.-%, for example, about 5 wt.-%.

The following table shows some examples for ratios of amounts at which ciclosporin A can be optimally solubilised in liposomal form:

| Ciclosporin A | Lipoid S 100 | Polysorbate 80 | Aqua purificata | NaCl |
|---|---|---|---|---|
| 0.1% | 0.9% | 0.07% | 98.77% | 8% |
| 1% | 9.0% | 0.7% | 87.7% | 8% |
| 5% | 45% | 3.5% | 38.5% | 8.0% |

The composition according to the invention has the advantage that it can contain a relatively high content of a poorly soluble ciclosporin in solubilised form. At the same time, the ciclosporin is taste masked which is particularly advantageous in all oral, oromucosal, nasal and pulmonary uses, as well as in the particularly preferred use of the preparation for the manufacture of a medicament for topical therapy of the skin, in the eye, nose and ear and especially for the prophylaxis or treatment of lung transplant rejection by inhalation.

The composition can contain further pharmaceutical adjuvants which are helpful and common in the intended application. Suitable adjuvants are known to the skilled person. For example, the composition can optionally contain pH-correcting agents in order to adjust the pH, such as physiologically acceptable bases, acids or salts, optionally as buffer mixtures. In this context, physiologically acceptable does not mean that one of the adjuvants must be tolerable on its own and in undiluted form, which would not be the case, for example, for sodium hydroxide solution, but means that it must be tolerable at the concentration in which it is contained in the preparation.

Suitable pH-correcting agents for adjusting the pH are to be selected, inter alia, with regard to the intended route of application. Examples for potentially useful adjuvants of this group are sodium hydroxide solution, basic salts of sodium, calcium or magnesium such as, for example, citrates, phosphates, acetates, tartrates, lactates etc., amino acids, acidic salts such as hydrogen phosphates or dihydrogen phosphates, especially those of sodium, moreover, organic and inorganic acids such as, for example, hydrochloric acid, sulphuric acid, phosphoric acid, citric acid, cromoglycinic acid, acetic acid, lactic acid, tartaric acid, succinic acid, fumaric acid, lysine, methionine, acidic hydrogen phosphates of sodium or potassium etc.

In one of the advantageous embodiments of the invention, the preparation is adjusted—with our without pH-correcting agent—to a neutral or acidic pH. Preferably, the pH is in the range of at most about 8.5 or in the range of about 2.5 to about 7.5. For pulmonary or parenteral application, a pH of about 4 to about 7.5 is preferred, provided that this is compatible with other requirements of the formulation such as, for example, stability aspects. Particularly preferred is a composition which is buffered with a phosphate buffer to a pH in the range of 6.7 to 7.5 and, especially, a range of 6.7 to 7.3, whereby the stability of the liposomal formulation can be markedly improved and the occurrence of undesirable lysolecithin during storage can be effectively reduced (see Example 4).

Furthermore, the preparation can contain osmotically active adjuvants in order to adjust it to a desired osmolality, which is important in certain applications such as for parenteral injection or for inhalation or other topical applications, in order to achieve good tolerability. Such adjuvants are frequently referred to as isotonizing agents even if their addition does not necessarily result in an isotonic composition, but in an isotonicity close to physiological osmolality in order to achieve the best possible physiological tolerability.

A particularly frequently used isotonizing agent is sodium chloride, but this is not suitable in every case. In an advantageous embodiment of the invention, the preparation contains no sodium chloride, except, of course, natural ubiquitous sodium chloride amounts which may also be contained in water of pharmaceutical quality. In another embodiment, the preparation contains an essentially neutral salt as isotonizing agent which is not sodium chloride, but, for example, a sodium sulphate or sodium phosphate. In this case, however, salts other than sodium salts are even more preferable. Thus, it is known that certain calcium and magnesium salts have a positive or supporting effect in the inhalation of active agent solutions, possibly because they themselves counteract the local irritations caused by the administration and because they have a bronchodilatory effect which is currently postulated in the clinical literature (for example Hughes et al., Lancet. 2003; 361 (9375): 2114-7) and/or because they inhibit the adhesion of germs to the proteoglycans of the mucosa of the respiratory tract so that the mucociliary clearance as the organism's natural defence against pathogens is supported indirectly (K. W. Tsang et al., Eur. Resp. 2003. 21, 932-938). Advantageous are, for example, magnesium sulphate, which has excellent pulmonary tolerability and can be inhaled without concern, as well as calcium chloride (1-10 mmol).

As an alternative to neutral mineral salts, physiologically acceptable organic adjuvants can be used as isotonizing agents. Particularly suitable are water-soluble substances with relatively low molecular weights, for example, having a molecular mass of less than 300, or more preferably of less than 200, and having a correspondingly high osmotic activity. Examples of such adjuvants are sugars and sugar alcohols, in particular, mannitol and sorbitol, xylitol, trehalose.

The amount of isotonizing agent to be used must be adjusted so that, taking into account the other components contained in the composition, an osmolality of at least 150 mosmol/l results. Further preferred is an osmolality in the range of about 150 to 800 mosmol/l. In further embodiments, the preparation has an osmolality of about 250 to about 600 mosmol/l, or of about 250 to 400 mosmol/l.

If the ciclosporin content is to be as high as possible and if an accordingly relatively high amount of solubility-enhancing adjuvants must be used, it may be assumed that, even without addition of a separate isotonizing agent, the osmolality of the composition will already lie within the desired range or above that range so that the use of an isotonizing agent will not be necessary.

Since the composition contains surfactants as solubility-enhancing agents, this will of course have an effect on the surface tension of the preparation. This may be relevant especially for pulmonary application. In a preferred embodiment, the preparation has a surface tension, under standard conditions, i.e., at room temperature and under normal pressure, of about 25 to 75 mN/m, in order to allow an efficient nebulisation with a high fraction of respirable droplets having a diameter of at most 5 µm when using common nebulisers.

However, if the preparation is to be adapted for use with specific types of nebulisers, the surface tension can be adjusted to specific values, for example, to about 30 to about 65 mN/m. Currently, a surface tension of about 30 to about 45 mN/m is even more preferred, although this can not always be achieved if other formulation parameters are of primary relevance. On the other hand, the surface tension should not be less than about 25 mN/m.

The surface tension reduced by a surfactant can be helpful in improving the spreadability of the aerosol in the lungs which can, in turn, have a positive effect on the efficacy of the administration.

In the case of application by inhalation, the viscosity of the composition can also be relevant. In an embodiment which is preferred for nebulisation, the composition according to the invention has a dynamic viscosity under standard conditions of about 1.0 to 3.0 mPa·s. In a further embodiment, the viscosity lies between 1.2 and 2 mPa·s.

Furthermore, the preparation can contain further common adjuvants such as stabilisers, antioxidants, taste-improving agents, flavours, sweeteners, colorants, etc. which are available to the skilled person for the formulation of preparations depending on the intended application.

The liposomal preparation according to the invention can be prepared by high-pressure homogenisation. For example, the water-soluble components can be provided in the form of an aqueous solution into which the ciclosporin is dispersed and liposomes are subsequently formed by a high-pressure homogenisation process, wherein the size and the polydispersity index of the liposomes can be adjusted by varying the pressure and the number of cycles.

The composition or the concentrate according to the invention are filled into single- or multiple-dosed containers, preferably under aseptic conditions. Suitable primary packaging are, for example, polypropylene or polyethylene vials (PP-PE-vials) and cycloolefin copolymer blisters (COC-blisters) or polytherephtalate blisters (PET-blisters). Alternatively, containers made from other polymers or copolymers can be used which are suitable for a blow-fill-seal-process or a thermoplastic process. Sealed plastic containers such as PP- or PE-vials can be formed, filled and sealed, for example, in an integrated process comprising a blow-fill-seal-procedure. The thus produced containers are especially suitable for liquid products having a volume of about 0.2 ml or more and small volumes are suitable for dropping into the eye and the ear. For applications in a nebuliser or for topical application to the skin, wherein varying amounts of active agents are required, volumes of 0.2 to 5 ml, preferably 0.5 to 5 ml, are ideally filled into the container. For optimal patient friendliness, they can be formed with a closure which is removable by twisting or folding and which is formed so as to avoid sharp edges and allow a drop-wise well-dosable release of the liquid.

Alternatively, the opening through which the liquid content can be withdrawn may be designed in such a way that it fits to a Luer-connection or a Luer-Lock-connection. Thus, the opening may be round and have a diameter which essentially corresponds to the outer diameter of a male Luer-connection. In this way, a common syringe with a Luer-connection might be tightly connected to the container, for example, in order to take up the contents of the container and to transfer it to a nebuliser, or in order to mix the contents of the container with the contents of the syringe and subsequently transfer it to a nebuliser. As a further alternative, the plastic container may be configured in such a way that, after removal of the closure element, it may be essentially tightly connected with the liquid input connector of a correspondingly adapted nebuliser so as to allow direct transfer of the preparation to the reservoir of the inhaler.

Plastic containers of this kind are also advantageous because they can easily be provided with embossings which will allow blind people to identify the product. This makes it possible to avoid the use of paper labels, which is desirable in order to prevent the migration of components of the adhesive, the paper or the printing ink through the container wall into the preparation. Furthermore, through such an embossing, important information can be made available to visually impaired patients. The embossing can contain various information, for example, a lot number, a best before date, a product identification, instructions for use or one or more volume or dosage markings. Especially in the case of paediatric patients, where flexible dosing according to age and height is frequently desirable, a plurality of volume markings can serve to facilitate the withdrawal of a desired dose without requiring further implements, thus reducing the risk of dosing errors.

In a further variant of the invention, there are provided multiple-dose containers which contain a preparation as described above and which are configured in such a way that they allow the aseptic withdrawal of a single dose. Thus, the multiple-dose container can be a glass or plastic container like a vial or an infusion bottle having a closure made of an elastomer which is pierceable with a cannula or it may be a complex container comprising a dosing and withdrawal device of the kind used for preservative free nasal sprays so that the preparation according to the invention need not contain a preservative and so that it can be sprayed into the nose or other body cavities or onto the skin as is known in applications for the treatment of athlete's foot. A preservative free pumping spray has great advantages especially in the treatment of psoriasis or neurodermatitis because the liposomes can be applied thereby to the damaged or inflamed skin in a homogeneous and hygienic fashion.

One of the particular advantages of multiple-dose containers in connection with the preparations for inhalation is the flexibility which makes it possible to individually adjust the dosage without problems and without having to discard substantial amounts of the preparation, as would be the case with single-dose containers after these have been opened. In hospitals and care institutions, patients can thus be treated simultaneously and particularly efficiently and potentially at reduced cost by individual dosage adjustment. Similarly, special requirements in the therapy of individual patients may thus be easily taken into account.

If the composition cannot be sterilised in the final container, it is preferably filled into the containers by use of an aseptic procedure.

For the preferred aerosolisation of the preparation, any nebuliser useable in therapy can in principle be used. The well-established jet nebulisers are in principle as suitable as more modern ultrasonic or piezo-electric nebulisers. The advantage of jet nebulisers is that they are already very common and can be obtained at relatively low cost. Many patients are already familiar with the use of common jet nebulisers. Some jet nebulisers of the newer generation (for example, PARI LC PLUS® and PARI LC SPRINT®) use mechanisms by which the nebulisation is adjusted to the breathing rhythm of the patient so that as high as possible a fraction of the aerosol generated is available for inhalation.

Particularly preferred, however, is the aerosolisation of the preparation by means of a modern piezo-electric or electronic vibrating membrane nebuliser, in particular, with a nebulizer of the eFlow™ type of PARI. The special advantage for the patient using this device (or a similar device) is the marked reduction in inhalation time compared to alternative methods. The device does not only aerosolise a larger amount of liquid per unit time, but it also generates an aerosol of particularly high quality having a high fraction of small respirable aerosol droplets with a narrow droplet size spectrum, typically with a geometric standard deviation <1.6. Other potentially suitable vibrating membrane nebulisers are, for example, the AeroNeb Pro or -Go, Propose or I-Neb devices.

Therapeutic success is critically dependent on the reliable and adequate availability of the active agent in the lungs. For patient convenience, this should be achieved within an acceptable period of time. Patients will generally prefer short inhalation times and inhalation times of more than about 10 minutes can have a negative impact on patients' compliance. It is also useful to conduct the inhalation either continuously or by means of a breath trigger or a guided breathing pattern, which is possible, for example, when using a nebuliser of the eFlow type in connection with an Akita inhalation device (of InaMed). Particularly preferred is a breathing manoeuvre comprising a slow deep inhalation over 4-10 seconds, a holding of the breath for up to 10 seconds followed by quick exhalation.

As may be seen in Example 4 and FIG. 1, the active agent is very evenly distributed in the lungs with central and peripheral deposition each amounting to about 50%, which is therapeutically useful. Excessive peripheral deposition would result in increased systemic absorption which is known, at high concentrations, to result in renal damage. Ideally, the ratio of central to peripheral deposition should, depending on the nature of the disease, for example, for the prevention of bronchiolitis obliterans and subsequent rejection of transplanted lungs, amount to a ratio of central to peripheral deposition of 30:70 or 50:50 or 70:30.

However, nasal, oral, ophthalmic, mucosal, parenteral or topical application of the composition according to the invention can, in individual cases, be advantageous, too. The administration may be affected by application, dropping, spraying onto or into the body, which, in initial tests on humans, proved to be particularly well tolerated.

Due to its immunosuppressive activity, ciclosporin can be used for quite diverse medical indications, for example, for the prophylaxis and therapy of transplant rejections after various transplantations (kidney, liver, heart, heart and lungs, pancreas, bone marrow etc.) prophylaxis and therapy of graft-versus-host-disease, therapy of endogenous uveitis, manifest non-infective uveitis intermedia or posterior, behcet-uveitis, serious and resistant psoriasis, especially of the plaque type, nephritic syndrome due to glomerular diseases such as minimal glomerular change, focal segmental glomerulorsclerosis or membranous glomerulornephritis, serious active rheumatoid arthritis, therapy resistant forms of long-lasting atopic dermatitis as well as other diseases which require local or systemic immune suppression, such as the treatment of asthma or eye diseases. According to new findings, ciclosporin also acts as a pump efflux inhibitor and thereby prevents cancerous cells from ejecting cytostatically active medicaments.

A further use of the composition according to the invention is in the prophylaxis or treatment of diseases of the skin, especially of psoriasis, neurodermatitis, eczema or rejection reactions after skin transplantations. Treatment may be carried out, for example, in the form of a pumping spray which is sprayed onto the affected parts of the skin.

As described above, a particularly preferred use of the composition according to the invention is in the prophylaxis and therapy of lung transplant rejection as well as the prevention or delay of bronchiolitis obliterans. This disease occurs in many cases also after a bone marrow transplantation or stem cell transplantation which is why inhalation is considered to be particularly suitable to prevent or treat diseases such as, for example, bronchiolitis obliterans. For this application, the composition is to be inhaled in the form of an aerosol. Compared to systemic therapy (for example, by oral administration), local therapy has the advantage that the active agent is applied directly to the site of action which, on one hand, can increase therapeutic efficacy and, on the other hand, reduces systemic stress on the organism and improves the tolerability of the therapy. Due to the liposomal incapsulation of the active agent and the size of the liposomes of, on average, at most 100 nm, the active agent can permeate particularly well from the respiratory tract through the pulmonary epithelial cell layer into the lung tissue and exert its effects there. In a further variant, liposomes with an average diameter of 30 to 80 nm are preferred.

In order to achieve efficient local inhalation therapy of the lungs, the preferred features discussed above should be selected with regard to the nebulizer used for the administration, in such a way that the preparation of an aerosol with as large as possible fraction of respirable droplets is preferred. In particular, the fraction of droplets below a limit of about 2-4 µm in diameter should be as large as possible. Particularly preferred is an electronic vibrating membrane nebuliser having a perforated stainless steel membrane comprising about 4000 pores of a defined size by which an aerosol with a defined particle spectrum can be generated quickly and efficiently (Martin Knoch & Manfred Keller: The customized electronic nebuliser: a new category of liquid aerosol drug delivery systems. Expert Opin. Drug Deliv. (2005) 2 (2): 377-390). The liposomal preparation according to the invention can be inhaled thereby without destruction of the liposomes either in a continuous or in a breath triggered or guided aerosol generation mode or via a breathing machine so that a high fraction of the active agent can be deposited in a targeted fashion in the lungs within a short period of time. The advantage of this inhalation system is, in particular, that the dose which can be inhaled from the mouth piece is greater than 50% and that up to 98% of the droplets generated have a diameter of less than 5 µm and that up to 80% have an average geometric diameter of less than 3.5 µm, so that the active agent can be deposited, in a targeted fashion, in the distal regions of the lungs at higher efficiency than with compressor-jet-nebulisers. The composition can comprise one or more further active agents. An additional active agent can be selected, for example, from the group of immunomodulators, interferons, steroidal and non-steroidal and anti-inflammatory agents, heparinoids, beta-agonists, anticholinergics, endothelin and phosphodiesterase inhibitors, antibiotics, antimycotics, antiviral substances and cytostatics. Alternatively, a combination therapy may be achieved if the composition according to the invention contains only ciclosporin as active agent, but is administered in combination with another preparation which contains another active agent.

The administration of the composition according to the invention, in particular, the administration by inhalation, can be carried out without premedication. In particular, the administration can be carried out without premedication with local anaesthetics such as, for example, lidocaine and/or without premedication with bronchodilators ("Bronchiodilatoren") such as, for example, salbutamol.

Preferably, the composition is sterile, especially when it is intended to be used for pulmonary, parenteral or ophthalmic application. Moreover, it is preferably essentially free of solid particles having a size of more than about 3 µm. It is advantageous if, for example, the entire active agent contained in the composition is present in liposomally solubilised form. Accordingly, solid particles of active agent should be essentially absent, especially solid particles of active agent having a diameter of more than about 500 nm. Preferable are compositions which are essentially free of solid particles of any substance having a diameter of more than 500 nm.

As indicated above, the composition can be used as medicament, for example for the prophylaxis and treatment of autoimmune diseases, skin diseases, after transplantations or diseases of the sensory organs (eyes, nose, ear), malaise and pulmonary diseases, for example, asthma, chronic obstructive bronchitis, parenchymal, fibrotic and interstitial lung diseases or inflammations, lung cancer, and preferably for the prevention and treatment of acute or chronic transplant rejection reactions and the diseases resulting therefrom such as bronchiolitis obliterans, especially after lung, heart, bone marrow or stem cell transplantations, especially preferred after lung transplantations. It may further be used to increase the efficacy of other medicaments, in particular, of cytostatics, where an additive or synergistic effect may be achieved with ciclosporin through the efflux pump inhibition effect.

The pharmaceutical composition according to the present invention provides, inter alia, the following advantages:

The preparation of the liposomes in a single-step process can, even at a large scale of up to 1000 kg, be carried out by means of high pressure homogenisation and sterilisation by subsequent sterile filtration at a pore diameter of 0.22 µm is possible.

The liposomes can diffuse well from the respiratory tract into the lung tissue.

In order to achieve a therapeutic effect, only 1-3, more preferably 1-2, inhalations per day are necessary.

The composition shows a depot effect at the target organ and, in certain cases, it must be inhaled only 1-4 times per weak, and particularly preferred, only every second day.

The composition can be stored in the fridge (4-8° C.) for at least 12 months, and particularly preferred, for up to 36 months.

The composition can also be used in breathing machines or in connection with systems for controlled breathing manoeuvres, such as the eFlow-Akita device.

Important aspects and embodiments of the invention will now be illustrated by way of the following examples.

Further embodiments are available to the skilled person by reference to the description and the patent claims.

Example 1: Solution for Topical Treatment for Spraying onto the Skin

|  | Concentration [w/w %] | Function |
| --- | --- | --- |
| Ciclosporin A | 0.50 | Active agent |
| Tween 80 | 0.35 | Solubility enhancer |
| Phospholipon G90 | 4.50 | Solubility enhancer |
| NaCl | 0.5 | Isotonizing agent |
| Dexpanthenol | 5.0 | Skin protective agent |
| Tocopherol acetate | 0.05 | Antioxidant |
| Sodium citrate | 0.05 | Buffer |
| Citric acid | 0.04 | Buffer |
| Water for injection | ad 100.0 | Solvent |

The water-soluble adjuvants (sodium chloride, sodium citrate, citric acid and Tween 80) listed in the above table are weighed into a 1 liter Erlenmeyer flask and are dissolved in water with stirring. Thereafter, the lecithin (Phospholipon G90), dexpanthenol, tocopherol acetate and the active agent (ciclosporin A) are added and dispersed with stirring. Thereafter, the mixture is homogenised for about 10 minutes in an Ultraturax and transferred to a high pressure homogeniser. At about 1500 bar, the mixture is homogenised until a colloidal preparation is obtained whose droplet or particle size in a Malvern Zetasizer has a diameter of <100 nm and a polydispersity index of <0.4. The colloidal preparation is subsequently sterile filtered under a clean bench and 20 ml thereof are filled into previously sterilized brown glass bottles which are closed with a pumping spray cap which allows multiple sterile withdrawal of the composition.

Example 2: Colloidal Solution for Inhalation

A colloidal preparation consisting of the components listed in the following table is prepared as described above and after sterile filtration 4 ml thereof are filled into 6 ml brown glass bottles which are closed. The content thereof is then transferred as needed, to the medicament reservoir of an electronic nebuliser such as, for example, the eFlow device of PARI, and the resulting aerosol can then be inhaled in order to avoid, for example, rejection reactions after lung transplants or the formation of a bronchiolitis obliterans.

|  | Concentration [w/w %] | Function |
| --- | --- | --- |
| Ciclosporin A | 0.50 | Active agent |
| Tween 80 | 0.35 | Stabiliser |
| Lipoid S100 | 4.5 | Carrier |
| NaCl | 0.85 | Isotonizing agent |
| Disodium edetate | 0.05 | Complexing agent |
| Water for injection | ad 100.0 | Solvent |

The pH of the clear, slightly opalescent liposomal solution at 20° C. was 4.5, the osmolality was 0.32 osmol/kg. Dynamic viscosity was measured to be 1.35 mPas; the surface tension was 36 mN/m.

The colloidal solution was nebulised with especially adapted vibrating membrane nebuliser of the eFlow type of PARI and the aerosols characterised by means of a PARI breathing simulator. This test involved two different inhalation manoeuvres, namely that of a child, 16 breaths per minute at a volume of 225 ml each, with a ratio of inhalation to exhalation of 40:60) and that of an adult (15 breaths per minute at a volume of 500 ml each, with a ratio of inhalation to exhalation of 1:1). The aerosol characteristics are given in the following table:

|  | Adult breathing pattern (15 breaths at 500 ml, inhalation:exhalation = 50:50) | | Child breathing pattern (16 breaths at 225 ml, inhalation:exhalation = 40:60) | |
| --- | --- | --- | --- | --- |
|  | Average | Standard deviation | Average | Standard deviation |
| Aerosol dose from the mouthpiece [μg] | 9577.1 | 745.1 | 8954.4 | 1085.8 |
| Nebuliser residue [μg] | 1606.8 | 559.2 | 2123.9 | 352.8 |
| Aerosol losses [μg] | 2872.5 | 255.9 | 2763.3 | 376.2 |
| Nebulisation time [min] | 9.5 | 0.6 | 11.6 | 1.4 |
| Aerosol dose [% of filling dose] | 66.5 | 4.5 | 62.9 | 8.4 |
| Nebuliser residue [% of filling dose] | 11.2 | 3.9 | 15.0 | 2.5 |
| Aerosol losses [%] | 20.0 | 2.0 | 19.4 | 2.5 |
| Recovery [% of filling dose] | 97.7 | 5.0 | 97.3 | 7.1 |

Moreover, using the same inhalation solution, the particle size fractions which are relevant for pulmonary administration were determined by laser diffraction measurement at various aerosol release rates (see following table). This showed particularly high efficiency of aerosol release and simulated deposition, which allow short inhalation time and which is largely independent of the inhalation manoeuvre.

|  | 15 L/min | | 20 L/min | | 28.3 L/min | |
| --- | --- | --- | --- | --- | --- | --- |
|  | Average | Standard deviation | Average | Standard deviation | Average | Standard deviation |
| Mass average diameter [μm] | 2.8 | 0.1 | 2.9 | 0.1 | 2.7 | 0.1 |
| Geometric standard deviation [ ] | 1.5 | 0.0 | 1.5 | 0.0 | 1.5 | 0.0 |
| Respirable fraction [% < 3.3μ] | 63.5 | 1.7 | 61.5 | 4.1 | 66.0 | 3.4 |
| Respirable fraction [% < 5μ] | 89.4 | 1.1 | 89.2 | 2.1 | 91.2 | 1.6 |
| Aearosol release rate [mg/min] | 289.0 | 10.8 | 258.3 | 40.3 | 282.5 | 28.0 |

The effect of the inhalation solution described in Example 2 on calu-3 cells (confluent monolayer) was investigated. For this purpose, calu-3 cells (HTB-55, ATCC, Manassas, Va., USA) were cultivated in Minimal Essential Medium (MEM) with Earl's salts, supplemented by L-glutamine (PAA Laboratories GmbH, Pasching, Austria), 10% fetal bovine serum, 1% nonessential amino acid solution and 55 mg/500 ml sodium pyruvate. The formation of confluent monolayers with tight junctions was confirmed by measurement of the trans-epithelial electrical resistance (TEER) using a suitable voltmeter (EVOM, World Precision Instruments, Berlin, Germany) and an STX-2 electrode. The age of the cell-monolayer during the tests with ciclosporin solution was about 14 days. At first, the culture medium was removed, the monolayer was washed and pre-incubated with Ringer hydrogen carbonate buffer solution for 20-30 minutes. Subsequently, the liposomal solution was added by means of a pipet.

The TEER was measured immediately after application and 120 min later. Thereafter, the cells were washed again and incubated with culture medium for 24 hours. Thereafter, the TEER was measured again. For comparison, Ringer hydrogen carbonate buffer solution (KRB), propylene glycol, a ciclosporin A solution in propylene glycol (62.5 mg/ml) and an aqueous sodium dodecyl sulphate solution (SDS) (0.1%) were used. The following table shows the measured TEER values as percentages of the initial values after addition of the Ringer hydrogen carbonate buffer solution.

| | TEER [% of 0 hours] | | | |
|---|---|---|---|---|
| Concentration [%, w/v] | Time [h] | Average (n = 3) | SD | RSD |
| Positive control (0.1% SDS) | Medium | 100 | | |
| | KRB | 107 | 2 | 2 |
| | 0 | 20 | 1 | 4 |
| | 1 | 19 | 1 | 7 |
| | 2 | 19 | 5 | 26 |
| | 24 | 11 | 1 | 7 |
| Negative control (KRB) | Medium | 100 | | |
| | KRB | 108 | 2 | 2 |
| | 0 | 101 | 6 | 5 |
| | 1 | 86 | 2 | 2 |
| | 2 | 83 | 0 | 0 |
| | 24 | 70 | 3 | 4 |
| Ciclosporin liposomes 5 mg/ml | Medium | 100 | | |
| | KRB | 115 | 1 | 1 |
| | 0 | 114 | 5 | 4 |
| | 1 | 95 | 4 | 4 |
| | 2 | 90 | 1 | 1 |
| | 24 | 92 | 2 | 2 |
| Ciclosporin liposomes 1:5 dilution in KRB | Medium | 100 | | |
| | KRB | 102 | 8 | 8 |
| | 0 | 88 | 8 | 10 |
| | 1 | 99 | 11 | 12 |
| | 2 | 108 | 13 | 12 |
| | 24 | 89 | 6 | 7 |
| Ciclosporin liposomes 1:10 dilution in KRB | Medium | 100 | | |
| | KRB | 119 | 7 | −25 |
| | 0 | 114 | 7 | −25 |
| | 1 | 143 | 7 | −25 |
| | 2 | 155 | 7 | −25 |
| | 24 | 122 | 7 | −25 |
| Ciclosporin liposomes 1:15 dilution in KRB | Medium | 100 | | |
| | KRB | 123 | 3 | 3 |
| | 0 | 119 | 7 | 6 |
| | 1 | 120 | 3 | 2 |
| | 2 | 135 | 4 | 3 |
| | 24 | 101 | 3 | 3 |

-continued

| | TEER [% of 0 hours] | | | |
|---|---|---|---|---|
| Placebo liposome concentrate | Medium | 100 | | |
| | KRB | 123 | 3 | 3 |
| | 0 | 124 | 5 | 4 |
| | 1 | 101 | 3 | 3 |
| | 2 | 102 | 4 | 4 |
| | 24 | 102 | 2 | 2 |
| Placebo liposome concentrate dilution 1:5 | Medium | 100 | | |
| | KRB | 111 | 5 | 5 |
| | 0 | 97 | 3 | 3 |
| | 1 | 96 | 5 | 5 |
| | 2 | 97 | 3 | 3 |
| | 24 | 97 | 6 | 6 |
| Placebo liposome concentrate dilution 1:10 | Medium | 100 | | |
| | KRB | 124 | 3 | 3 |
| | 0 | 102 | 3 | 3 |
| | 1 | 99 | 2 | 2 |
| | 2 | 119 | 1 | 1 |
| | 24 | 84 | 5 | 6 |
| Placebo liposome concentrate dilution 1:15 | Medium | 100 | | |
| | KRB | 132 | 2 | 1 |
| | 0 | 115 | 14 | 12 |
| | 1 | 110 | 7 | 6 |
| | 2 | 121 | 9 | 7 |
| | 24 | 80 | 1 | 1 |

| | | TEER after 2 h | | TEER after 24 h | |
|---|---|---|---|---|---|
| Test preparations | Conc. [%] | Average [%] | SD | Average [%] | SD |
| KRB | | 134 | 19.87 | 89 | 18.35 |
| CSA/propylene glycol | 11.050 | 9 | 2.46 | 22 | 4.65 |
| Propylene glycol | 10.000 | 14 | 2.42 | 43 | 2.71 |
| | 5.000 | 36 | 8.75 | 75 | 10.36 |
| | 0.500 | 120 | 12.82 | 83 | 8.77 |
| | 0.100 | 116 | 3.80 | 83 | 3.90 |
| SDS (sodium dodecyl sulphate) | 0.100 | 3 | 1.93 | 2 | 1.25 |
| | 0.010 | 7 | 0.80 | 2 | 0.37 |
| | 0.001 | 114 | 20.30 | 107 | 16.29 |

The measured TEER values show that the composition according to the present invention has no or only a small and largely reversible effect on the integrity of the calu-3 monolayer. Sodium dodecyl sulphate (SDS, synonym: sodium lauryl sulphate), propylene glycol and ciclosporin A dissolved in propylene glycol, on the other hand, produce significant and largely non-reversible damage to the calu-3 cell monolayer. From this, it can be concluded, among other things, that propylene glycol is probably not a suitable carrier for ciclosporin A for application by inhalation.

Example 3: Colloidal Solution

The following formulations A and B (see following tables) were prepared in a fashion similar to that described in Example 1 and filled into brown glass bottles under sterile conditions.

| Example 3, formulation A | Concentration [wt.-%] |
|---|---|
| Ciclosporin A | 0.50 |
| Tween 80 | 0.35 |
| Lipoid S100 | 4.50 |
| Sodium dihydrogen phosphate monohydrate | 0.215 |
| Sodium hydrogen phosphate dodecahydrate | 0.34 |
| Sodium chloride | 0.80 |
| Disodium edetate | 0.02 |
| Water for injection | ad 100.0 |

| Example 3, formulation B | Concentration [wt.-%] |
|---|---|
| Ciclosporin A | 0.40 |
| Tween 80 | 0.28 |
| Lipoid S100 | 3.60 |
| Sodium dihydrogen phosphate monohydrate | 0.215 |
| Sodium hydrogen phosphate dodecahydrate | 0.34 |
| Sodium chloride | 0.80 |
| Disodium edetate | 0.02 |
| Water for injection | ad 100.0 |

The colloidal solutions are suitable, in particular, for inhalation. Furthermore, they may be used for topical and ophthalmic applications.

Example 4: Colloidal Solution

The following formulation (see following table) was prepared in a fashion analogous to that described in Example 1 and the filling procedure was performed under sterile conditions.

| Example 4, formulation | Concentration [wt.-%] |
|---|---|
| Ciclosporin A | 0.50 |
| Tween 80 | 0.35 |
| Lipoid S100 | 4.50 |
| Vitamin E TPGS | 0.35 |
| Sodium dihydrogen phosphate monohydrate | 0.25 |
| Sodium hydrogen phosphate dodecahydrate | 0.25 |
| Sodium chloride | 0.85 |
| Disodium edetate | 0.02 |
| Water for injection | ad 100.0 |

The slightly opalescent solution was subsequently characterized; the results are shown in the following table.

| Parameter | Value |
|---|---|
| pH | 6.51 |
| Dynamic viscosity | 1.36 mPas * s |
| Surface tension | 32.8 mN/m |
| Refractive index | 1.342 |
| Osmolality | 372 mosmol/kg |
| Density | 1.007 g/cm$^3$ |
| Median liposome diameter | 35.7 nm |
| Polydispersity index | 0.21 |

Furthermore, the actual content of CsA was measured to be 4.83 mg/ml. The content of impurities was 0.81 mg/ml.

After storage at 5° C. for three months, all parameters were essentially unchanged, including, for example, the CsA content (4.93 mg/ml), the content of impurities (0.36 mg/ml) as well as the median liposome diameter (36.6 nm). After storage at 25° C. and 60% relative humidity for three months, the preparation still proved to be remarkably stable; in particular, the content of CsA and impurities remained essentially constant. The median liposome diameter was slightly increased to 44.4 nm; however, this should have no impact on the performance of the composition.

3.2 ml (corresponding to 15 mg of CsA) of the colloidal solution were aerosolised by means of a specially adapted electronic vibrating membrane nebuliser of the PARI eFlow 30 L type having a mixing chamber and breathing in/out valves and the droplet size distribution of the thus produced aerosol was characterised by laser diffraction using a Malvern MasterSizerX at a flow rate of 20 l/min. The mass average particle diameter thus determined was 2.8 μm at a geometric standard deviation of 1.5. The particle fraction <5 μm (respirable fraction) was 89.4%, the fraction having a particle size <3.3 μm was 63.5%. The total output rate was 289 mg/ml.

Figure 3:
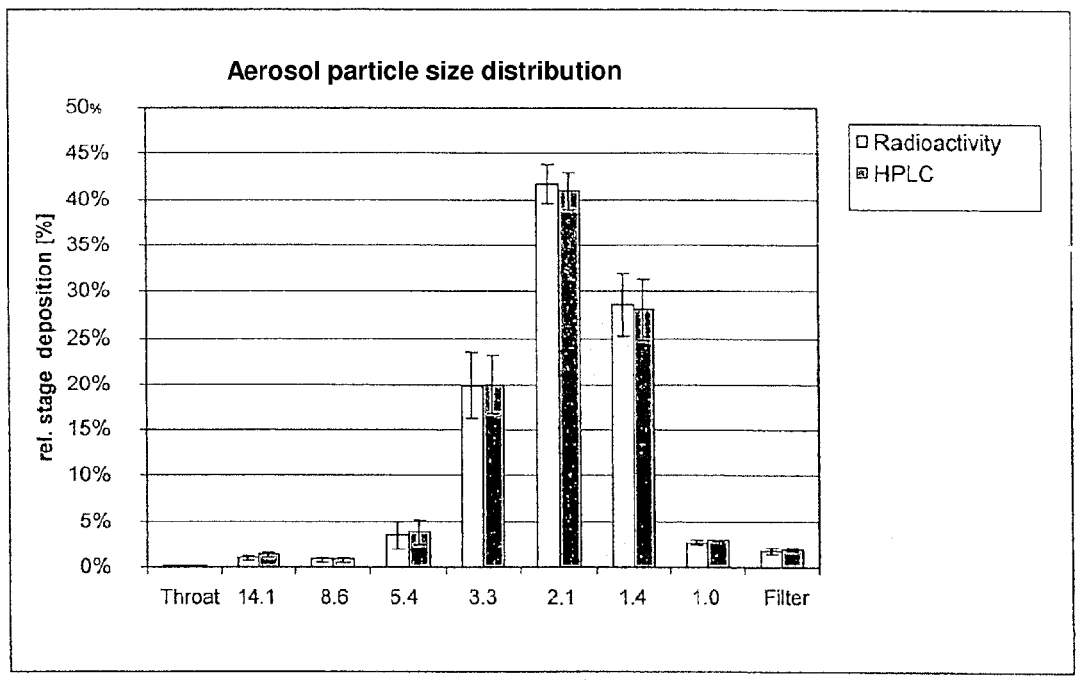
FIG. 3 shows the distribution of aerosol fractions of the cyclosporine A containing formulation of Example 4 over the individual impactor stages of a next generation cascade impactor connected to a PARI breath simulator, as obtained in a breathing simulation test wherein the typical inhalation pattern of an adult was applied as described in Example 4 and the aerosol was generated with an electronic vibrating membrane nebuliser of the PARI eFlow 30L type. The cyclosporine A fractions were determined either by HPLC measurements or, after nebulising a radio-labelled formulation, by radioactivity measurements.

Furthermore, the aerosol was characterised in a breathing simulation test using a PARI breath simulator using the typical inhalation pattern on an adult (see Example 2) as well as a cascade impactor of the next generation impactor type at a flow rate of 15 l/min, a temperature of 23° C. and a relative humidity of 50%. The aerosol characteristics thus determined are shown in the following table. The inhalation time was 11 minutes. The determination of the CsA fractions was done after determination of the content of the active agent by HPLC. In a further test, the inhalation solution was radio-labelled with $^{99}$mTc-DTPA, subjected to the same experimental setup and the aerosol characteristics were determined from the radioactivity of the deposited fractions. The results of both experiments were essentially identical. FIG. 3 shows the distribution of aerosol fractions over the individual impactor stages (based on radioactivity measurement and HPLC), the values on the abscissa being shown in units of μm.

| Parameter | mg | % |
|---|---|---|
| Initial (filling) amount of CsA | 15.0 | 100 |
| Delivered dose of CsA | 11.4 | 75.9 |
| Amount of CsA remaining in the inhaler | 1.3 | 8.5 |
| Aerosol loss of CsA | 2.0 | 13.1 |

Using the composition, there was also carried out a gamma-scintigraphy-study to determine the pulmonary deposition of CsA in vivo. For this purpose, 12 patients with lung transplants (7 with double-sided [DLTx] and 5 with single-sided transplants [SLTx]) were treated with 2 ml (about 10 mg of CsA) of the inhalation solution. Each dose of inhalation solution administered was previously radio-labelled with 4 MBq 88 mTc-DTPA (Pentacis, CIS-Diagnostik) and subsequently filled into an electronic vibrating membrane nebuliser of the PARI eFlow 30L type. Patients were instructed to inhale slowly and deeply. After the nebulisers' reservoir was empty, the head and chest region of the patients was imaged using a gamma-camera of the Siemens Diacam type.

Figure 2:
FIG. 2 shows a typical gamma-scintigraphy image from a patient with single-sided lung transplant after treatment with a radio-labelled dose of the cyclosporine A containing formulation of Example 4, which was nebulised with an electronic vibrating membrane nebuliser of the PARI eFlow 30L type.

FIG. 1 shows a typical image from a treated patient with double-sided lung transplant; FIG. 2 shows the image of a patient with single-sided transplant. The image shows the even deposition of the fine aerosol in the lungs. The inhalation was well tolerated by all patients; premedication, as used according to the literature in the inhalation of known CsA preparations, wherein the active agent was dissolved in propylene glycol, was not necessary.

In a further experiment with the same patients, a dose of 4 ml at the same concentration of active agent was administered. This dose, too, was tolerated without premedication.

The quantitative determination of radioactivity showed an average lung deposition of 36% of the CsA dose filled into the nebuliser. The relative deposition in the lungs was slightly higher in the case of the lower dose of 2 ml than for the higher dose of 4 ml. The following table summarises the results.

| Site of deposition | Average (all) | 2 ml | 4 ml | DLTx | SLTx |
|---|---|---|---|---|---|
| Intrapulmonary | 36.0% | 39.8% | 32.6% | 37.0% | 36.0% |
| (thereof peripheral) | 19.0% | 20.4% | 17.2% | 20.0% | 18.0% |
| Extrathoracic | 15.0% | 16.3% | 13.6% | 14.0% | 15.0% |
| Residue in nebuliser | 18.0% | 10.1% | 26.4% | 19.0% | 18.0% |

-continued

| Site of deposition | Average (all) | 2 ml | 4 ml | DLTx | SLTx |
|---|---|---|---|---|---|
| Aerosol loss/exhaled | 3.01% | 33.9% | 27.4% | 31.0% | 31.0% |
| Inhalation time | | 9.0 min | 19.1 min | | |

Furthermore, the pharmacokinetic parameters for the administration of 10 mg or 20 mg CsA by inhalation were determined by blood analysis. The results thus obtained are given in the following table.

| | 10 mg | 20 mg | |
|---|---|---|---|
| $T_{1/2}$ | 5.2 h | 6.1 h | p = 0.034 |
| AUC | 110 h · ng/ml | 190 h · ng/ml | p = 0.025 |
| $c_{max}$ | 20 ng/ml | 31 ng/ml | |
| MRT (mean residence time) | 7.8 h | 8.6 h | no sig. |

Surprisingly, it was found that only a small proportion of the liposomal CsA inhalation solution is found in the blood and that the half-life is very short at 5.2 and 6.1 hours, respectively.

Previously published data (Corcoran T E et al.: Preservation of post-transplant lung function with aerosol cyclosporin. Eur. Respir. J., 23(3), 378-83 (2004)) referred to a half-life of about 40 hours after inhalation of 300 mg of CsA/propylene glycol inhalation solution. The advantage of the short half-life lies in the possibility of frequent administration, for example, once or twice a day. In this way, it will be possible to achieve even therapeutic levels also in the lungs and this will result in a reliable therapy.

Moreover, there was found to exist a correlation between the peripherally deposited CsA dosis and the pharmacological parameters AUC (area under the curve) and $c_{max}$ (maximum concentration) for the liposomal CsA therapy: this makes it possible to provide an estimate of the CsA active concentration in the target area of the target organ, i.e., in the periphery of the lungs, by simply measurement of the serum levels of the patient concerned. This allows simple monitoring of the therapy.

Example 5: Colloidal Solution for Dropping into the Eye

A colloidal preparation of the ingredients listed in the following table is prepared as described above and, after sterile filtration, 0.25 ml thereof are filled, under aseptic conditions and laminar air flow, into sterile, pear-shaped 0.5 ml polyethylene blow fill seals vials (PE) formed with sterile nitrogen and subsequently sealed into aluminium blisters under nitrogen gas. From these sterile unit dose vials which allow drop-wise product withdrawal, the colloidal solution can be dropped into the eye in order to treat, for example, rejection reactions after corneal transplantations and other inflammatory processes.

| | Concentration [w/w %] | Function |
|---|---|---|
| Ciclosporin A | 0.50 | Active agent |
| Tobramycin | 1.0 | Active agent |
| Tween 80 | 0.35 | Stabiliser |
| Lipoid S100 | 4.50 | Carrier |
| NaCl | 0.56 | Isotonizing agent |
| $KH_2PO_4$ | 0.68 | Buffering substance |
| Sodium hydroxide | q.s. | Buffering substance |
| Disodium edetate | 0.05 | Complexing agent |
| Water for injection | ad 100.0 | Solvent |

Example 6

0.2 g of each of ciclosporin A and tacrolimus are dispersed in a liposomal isotonic placebo solution containing lecithin and polysorbate 80 at a weight ratio of 10:1 in an isotonic sodium chloride solution by means of an Ultraturax and subsequently homogenised under high pressure in a microfluidizer at 1500 bar so that, in a Malvern Zetasizer, a colloidal preparation with a diameter of less than 80 nm and a polydispersity index <0.35 is obtained. After sterile filtration, portions of 2 ml are filled, under aseptic conditions and laminar air flow into sterile polyethylene blow fill seal vials (PE) formed with sterile nitrogen and are subsequently sealed ("eingeschweißt") into aluminium blisters under nitrogen gas. From these sterile unit dose vials which allow drop-wise product withdrawal, the colloidal solution can be used for pulmonary, nasal or topical application in order to treat undesired autoimmune diseases.

Example 7: Liposomal Solution for Inhalation or for Application at the Eye or Ear Into an isotonic, colloidal-disperse placebo solution prepared by high-pressure homogenisation and consisting of 10% Lipoid S100, 0.7% polysorbate 80, 0.8% sodium chloride and 0.01% of sodium-EDTA and tocopherol acetate, respectively, there are dispersed 0.4% ciclosporin A and 0.04% budesonide and these are incorporated in colloidal-disperse form so that a liposomal preparation having a diameter <75 nm, a polydispersity index <0.3 is obtained. Under a transmission electron microscope, one can see spherical unilamellar liposomal structures of 55-75 nm, which correlate well with results of 40-55 nm determined by photon correlation spectroscopy (PCS). After sterile filtration, portions of 0.25 ml for treatment of the eyes and ears and portions of 2 ml for use in nebulisers are filled into polypropylene vials filled with nitrogen gas and, for storage stability, these are sealed separately into nitrogen gas-filled aluminium blisters. After nebulisation with an electronic eFlow nebuliser, the product is inhaled for the treatment of pulmonary diseases such as, for example, asthma and COPD.

Example 8

Into an isotonic, colloidal-disperse placebo solution prepared by high-pressure homogenisation and consisting of 40% Lipoid S100 and 2% of each of polysorbate 80 and vitamin E-TPGS, 0.8% of sodium chloride and 0.02% of sodium-EDTA, there are dispersed 1.5% ciclosporin A and sirolimus (rapamycin), respectively, and incorporated in colloidal-disperse form so that a liposomal preparation having a diameter <100 nm and a polydispersity index <0.3 is obtained. After sterile filtration, portions of 2 ml are filled into nitrogen gas-filled polyethylene vials and, for greater storage stability, sealed separately into aluminium blisters filled with nitrogen gas. The product is used for inhalation to treat interstitial pulmonary diseases such as sarcoidosis and pulmonary fibrosis. Alternatively, it can be used for dropping into the eye after corneal transplantations.

Example 9: Colloidal Solution for Topical Treatment of the Skin, Eye and Ear

| | Concentration [w/w %] | Function |
| --- | --- | --- |
| Ciclosporin A | 0.50 | Active agent |
| Tween 80 | 0.35 | Stabiliser |
| Lipoid S100 | 4.50 | Solubility enhancer |
| NaCl | 0.5 | Isotonizing agent |
| Dexpanthenol | 5.0 | Skin protection agent |
| Disodium edetate | 0.05 | Complexing agent |
| Water for injection | ad 100.0 | Solvent |

The water-soluble adjuvants listed in the above table are weighed into a 1 liter Erlenmeyer flask and dissolved in water with stirring; thereafter, the lecithin (Lipoid S100 or Phospholipon G90) and the active agent (ciclosporin) are added and dispersed with stirring. Subsequently, the mixture is homogenised for 10 min in the Ultraturax and transferred to a high-pressure homogeniser. At about 1500 bar, this mixture is homogenised until a colloidal preparation is obtained whose droplet or particle size in a Malvern Zetasizer has a diameter of <100 nm and a polydispersity index of <0.4. The colloidal preparation is subsequently sterile filtered under a clean bench and filled into previously sterilised brown glass bottles having a volume of 5-50 ml which are subsequently closed with a sterile pumping dosing cap which allows drop-wise multiple withdrawal of parts of the content.

Example 10

Into an isotonic, colloidal-disperse placebo solution prepared by high-pressure homogenisation and consisting of 40% Phospholipon and 2% of each of polysorbate 80 and vitamin E-TPGS, 0.8% of sodium chloride and 0.02% of sodium-EDTA, there are dispersed 3% of dexpanthenol and 1% of each of ciclosporin A, amphotericin B and incorporated in colloidal-disperse form so that a liposomal preparation having a diameter <100 nm and a polydispersity index <0.3 is obtained. After sterile filtration, portions of 2 ml are filled into nitrogen gas-filled polyethylene vials and, for greater storage stability, sealed separately into aluminium blisters filled with nitrogen gas. The product is used for the prevention and treatment by inhalation of possible rejection reactions after transplantations of organs or organ parts such as the lungs, nose, skin, cornea, ear and diseases resulting therefrom.

Example 11

Into an isotonic, colloidal-disperse placebo solution prepared by high-pressure homogenisation and consisting of 20% Phospholipon and 1% of each of polysorbate 80 and vitamin E-TPGS, 0.8% of sodium chloride and 0.02% of sodium-EDTA, there are dispersed 2% of each of hyaluronic acid as well as sodium chromoglycate and 1% of ciclosporin A and incorporated in colloidal-disperse form so that a colloidal-disperse preparation having a diameter <100 nm and a polydispersity index <0.3 is obtained. After sterile filtration, portions of 2 ml are filled into nitrogen gas-filled polyethylene vials and, for greater storage stability, sealed separately into aluminium blisters filled with nitrogen gas. The product is used for the prevention and treatment by inhalation of chronic obstructive bronchitis, parenchymal, fibrotic and interstitial pulmonary diseases or inflammations as well as topically for the suppression of autoimmune diseases and for healing wounds of the skin, the nose and the ear.

Example 12

In a fashion analogous to that of Example 2, a liposomal inhalation solution containing ciclosporin A (4.5 mg/ml), phospholipid (Lipoid S100, 40 mg/ml), polysorbate 80 (Tween 80, 3 mg/ml), sodium chloride (8.5 mg/ml) and disodium edetate (0.5 mg/ml) was prepared. The homogenisation was carried out by means of a high-pressure homogeniser at 1500 bar and 2 cycles. The average particle size of the liposomes was 50 nm (measured as z-average) at a polydispersity index of about 0.25. The liposomes (portions of 2 ml) were, after sterile filtration under aseptic conditions, filled into specially formed 3 ml vials which could be tightly connected to the twist-and-pull cap of an eFlow. When closing the medicament recipient device, the membrane of the PE-vial is broken so that the contents can be inhaled without manually filling them into the nebuliser.

Example 13

The liposomal formulation can also be combined with water-soluble active agents, as can be seen from the following example. The water-soluble adjuvants are weighed into a 200 liter vessel according to the composition by weight-percent given in the following tables and dissolved with stirring in water for injection. The water-soluble active agents such as, for example, heparin sodium (formulation A) or salbutamol sulphate (formulation B) are then dissolved therein, lecithin and the lipophilic ciclosporin A are added and dispersed with stirring and the mixture is subsequently homogenised for 10 min in an Ultraturax and transferred to a high-pressure homogeniser. This mixture is homogenised in 5 cycles under high-pressure of about 1000 bar. Thereafter, a sample is withdrawn and the specification is checked according to the in-process control. When the droplet or particle size, measured in a Malvern Zetasizer, is <100 nm and has a polydispersity index of <0.35, the colloidal preparation is sterile filtered. Portions of 2 ml thereof are filled into polyethylene ampoules using an aseptic filling process in a sterile room according to a blow-fill process and 5 pieces thereof are sealed into aluminium blisters filled with nitrogen gas.

| Example 13, formulation A | Concentration [w/w %] |
| --- | --- |
| Ciclosporin A | 0.40 |
| Tween 80 | 0.28 |
| Phospholipon G90 | 3.60 |
| NaCl | 0.5 |
| Heparin sodium | 2.0 |
| Sodium chloride | 0.025 |
| Water for injection | ad 100.0 |

| Example 13, formulation B | Concentration [w/w %] |
| --- | --- |
| Ciclosporin A | 0.40 |
| Tween 80 | 0.28 |
| Lipoid S100 | 3.60 |
| NaCl | 0.5 |
| Salbutamol sulphate | 0.50 |
| Sodium edetate | 0.05 |
| Water for injection | ad 100.0 |

The invention claimed is:

1. A method for treating a subject suffering from or susceptible to asthma; refractory asthma; chronic obstructive bronchitis; parenchymal, fibrotic, or interstitial lung disease and/or inflammation; lung cancer; acute or chronic lung transplant rejection; undesired reaction after lung, stem cell, or bone marrow transplantation and the diseases resulting therefrom; the method comprising:
   (a) providing a composition comprising a cyclosporin in liposomally solubilised form, an aqueous carrier liquid, a first solubility enhancing substance selected from the group of phospholipids and a second solubility enhancing substance selected from the group of nonionic surfactants, wherein the phospholipid is a mixture of natural phospholipids and
   (b) administering a volume of less than 4 ml of the composition to the subject as an aerosol for pulmonary or nasal application, wherein the volume comprises a therapeutically effective dose of the cyclosporin.

2. The method of claim 1 wherein the subject suffers from or is susceptible to bronchiolitis obliterans.

3. The method of claim 1 wherein the composition is administered as an aerosol generated with an electronic vibrating membrane nebuliser.

4. The method of claim 1 wherein the composition comprises from about 0.5 to about 10 mg/ml of cyclosporin.

5. The method of claim 1 wherein the composition is administered once or twice daily.

6. The method of claim 1 wherein the generation of an aerosol containing 4 mg of cyclosporin in droplets of <5 μm requires less than 10 minutes.

7. The method of claim 1 wherein the rate at which the cyclosporin is inhaled from the mouth piece is 0.2-4 mg/min.

8. The method of claim 1 wherein the percentage of aerosol droplets of <5 μm is between 50% and 98% and the droplet distribution has a geometric standard deviation <2.2.

9. The method of claim 1 wherein the percentage of aerosol droplets of <3.5 μm is between 40% and 95%.

10. The method of claim 1 wherein the pulmonary deposition is at least 30% and the ratio of central to peripheral deposition is from 30:70-70:30.

11. The method of claim 1 wherein the dose inhalable by means of a mouth piece is >40% of the dose of active agent filled into the nebuliser.

12. The method of claim 1 wherein the residue of active agent remaining in the nebuliser is <20%.

13. The method of claim 1 wherein the nebulisation time is <15 minutes.

14. The method of claim 1 wherein the administration of the composition is carried out without premedication.

15. The method of claim 14 wherein the administration of the composition is carried out without premedication with a local anaesthetic.

16. The method of claim 14 wherein the administration of the composition is carried out without premedication with a bronchodilator.

17. The method of claim 1 wherein the composition is administered as part of a combination therapy together with at least one medicament which comprises an active agent selected from the group consisting of immunomodulators, interferons, steroidal and non-steroidal anti-inflammatory agents, heparinoids, beta-agonists, anticholinergics, endothelin and phosphodiesterase inhibitors, antibiotics, antimycotics, antiviral substances and cytostatics.

18. The method of claim 7 wherein the rate at which the cyclosporin is inhaled from the mouth piece is 0.5-1.5 mg/min.

19. The method of claim 8, wherein the percentage of aerosol droplets of <5 μm is between 60% and 90% and the droplet distribution has a geometric standard deviation <1.8.

20. The method of claim 9 wherein the percentage of aerosol droplets of <3.5 μm is between 50 and 85%.

* * * * *

UNITED STATES PATENT AND TRADEMARK OFFICE
CERTIFICATE OF CORRECTION

PATENT NO. : 9,724,382 B2
APPLICATION NO. : 13/693147
DATED : August 8, 2017
INVENTOR(S) : Manfred Keller, Aslihan Akkar and Ralf Mehrwald Page 1 of 1

It is certified that error appears in the above-identified patent and that said Letters Patent is hereby corrected as shown below:

On the Title Page

Item (62), following '9,161,963', insert --, a National Stage Entry of PCT/EP2006/011459, filed on Nov. 29, 2006--

Signed and Sealed this
Twenty-third Day of June, 2020

Andrei Iancu
*Director of the United States Patent and Trademark Office*